(12) United States Patent
Criere et al.

(10) Patent No.: US 8,409,612 B1
(45) Date of Patent: *Apr. 2, 2013

(54) MICROGRANULES INSOLUBLE IN GASTRIC FLUID, METHOD FOR OBTAINING SAME AND PHARMACEUTICAL PREPARATIONS

(75) Inventors: Bruno Criere, Gravigny (FR); Pascal Suplie, Montaure (FR); Pascal Oury, Le Chesnay (FR)

(73) Assignee: Ethypharm, Saint-Cloud (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/979,146

(22) PCT Filed: May 19, 2000

(86) PCT No.: PCT/FR00/01367

§ 371 (c)(1),
(2), (4) Date: Jan. 25, 2002

(87) PCT Pub. No.: WO00/71121

PCT Pub. Date: Nov. 30, 2000

(30) Foreign Application Priority Data

May 21, 1999 (FR) .................................. 99 06479

(51) Int. Cl.
*A61K 9/20* (2006.01)
(52) U.S. Cl. ........ 424/464; 424/451; 424/489; 424/490; 424/497; 424/472
(58) Field of Classification Search .................. 424/451, 424/464, 489, 490, 497, 498
See application file for complete search history.

(56) References Cited

U.S. PATENT DOCUMENTS

| | | | | |
|---|---|---|---|---|
| 4,153,677 A * | 5/1979 | John | ............................. | 424/495 |
| 4,572,833 A * | 2/1986 | Pedersen et al. | ............... | 424/467 |
| 5,288,506 A * | 2/1994 | Spickett et al. | ................ | 424/498 |
| 5,385,739 A | 1/1995 | Debregeas et al. | | |
| 5,654,009 A * | 8/1997 | Hata et al. | ...................... | 424/490 |
| 5,711,967 A * | 1/1998 | Juch | ............................... | 424/462 |
| 5,753,265 A * | 5/1998 | Bergstrand et al. | ............ | 424/474 |
| 5,834,004 A * | 11/1998 | Upmeyer et al. | .............. | 424/423 |
| 6,013,280 A * | 1/2000 | Frisbee et al. | ................. | 424/464 |
| 6,113,941 A * | 9/2000 | Takada et al. | ................. | 424/451 |
| 6,129,933 A * | 10/2000 | Oshlack et al. | ............... | 424/495 |
| 6,328,993 B1 * | 12/2001 | Linder et al. | .................. | 424/451 |
| 6,551,621 B1 * | 4/2003 | Debregeas et al. | ........... | 424/493 |

FOREIGN PATENT DOCUMENTS

| | | |
|---|---|---|
| EP | 0 342 522 B1 | 12/1991 |
| EP | 0 769 938 B1 | 10/1998 |
| EP | 1 010 423 A2 | 6/2000 |
| JP | 10029937 A * | 2/1998 |
| WO | WO 93/25204 A | 12/1993 |
| WO | 96/01624 * | 1/1996 |
| WO | WO 96/01624 A | 1/1996 |
| WO | 96/31213 A1 | 10/1996 |
| WO | WO 9631213 A1 * | 10/1996 |
| WO | 97/12581 A2 | 4/1997 |
| WO | WO 9712581 A2 * | 4/1997 |
| WO | 98/19668 A1 | 5/1998 |
| WO | 98/52564 * | 11/1998 |
| WO | WO 98/52564 A | 11/1998 |
| WO | 99/06032 * | 2/1999 |
| WO | 99/32091 A1 | 7/1999 |
| WO | 99/32093 A1 | 7/1999 |
| WO | WO 99/38511 A | 8/1999 |

OTHER PUBLICATIONS

The Merck Index, "An Encyclopedia of Chemicals and Drugs", Ninth Edition, 1976, p. 1099.*
Chemical Abstracts No. 187185, vol. 130, No. 14 (1999).
International Search Report for PCT/FR00/01367, dated Aug. 30, 2000.

* cited by examiner

*Primary Examiner* — Lakshmi Channavajjala
(74) *Attorney, Agent, or Firm* — RatnerPrestia

(57) ABSTRACT

A pharmaceutical formulation of a gastric proton pump inhibitor, with the exception of omeprazole, is disclosed. The formulation is in the form of microgranules insoluble in gastric fluid having improved stability over time. The formulation comprises several hydrophobic substances chosen in order to increase the stability of the active principle while obtaining the desired dissolution profile.

22 Claims, No Drawings

MICROGRANULES INSOLUBLE IN GASTRIC FLUID, METHOD FOR OBTAINING SAME AND PHARMACEUTICAL PREPARATIONS

The present invention relates to a pharmaceutical formulation of a gastric proton pump inhibitor, with the exception of omeprazole. This formulation is in the form of microgranules insoluble in gastric fluid having an improved stability over time.

The present invention additionally applies to the process for the manufacture of said microgranules and to the pharmaceutical preparations comprising them.

The gastric proton pump inhibitors coming within the scope of the present invention are benzimidazole or thienoimidazole derivatives, with the exception of omeprazole, and their pharmaceutically acceptable salts.

The proton pump inhibitors coming within the scope of the present invention include in particular lansoprazole, pantoprazole, perprazole, pariprazole, leminoprazole, timoprazole and their pharmaceutically acceptable salts.

Proton pump inhibitors are known for the treatment and prevention of diseases relating to excessive secretion of gastric acid, such as esophagitis, gastritis, duodenitis, gastric ulcer and duodenal ulcer.

These compounds can also be used in patients who are following an anti-AIDS therapy and in patients suffering from gastroesophageal reflux or from gastrinoma.

Finally, these compounds are of use in the treatment of psoriasis and infections caused by *Helicobacter*.

The benzimidazole derivatives of the invention are compounds capable of decomposing in acidic or neutral medium, with the result that a formulation comprising them must be:

enteric, in order for the active principle to reach the small intestine, and
  protected against heat, moisture, organic solvents and light, to a lesser extent.

The present invention relates to a novel formulation insoluble in gastric fluid of a proton pump inhibitor comprising at least two hydrophobic substances, the role of which is to improve the stability of the formulation on storage.

Formulations comprising a benzimidazole derivative and a hydrophobic substance already exist in the prior art but this substance is not particularly used to increase the stability of the formulation. In addition, these formulations comprise alkaline compounds and/or ionic surfactants.

WO 96/01624 discloses tablets formed from enteric microgranules comprising a proton pump inhibitor. The object of the invention disclosed is to prepare microgranules which can be tableted without modifying the properties of their enteric layer. To obtain the desired mechanical properties, the enteric layer must comprise plasticizers, such as polysorbates, PEGs and cetyl alcohol. The enteric layer is, for example, composed of 74-80% of a methacrylic copolymer, 16-23% of triethyl citrate and 1-3% of a monoglycerides/diglycerides mixture. WO 96/01624 discloses the use of a specific plasticizer in the enteric layer for improving the ability of the granules to be tableted. In addition, the compositions disclosed comprise an ionic surfactant, such as sodium lauryl sulfate, or an alkaline salt, such as calcium phosphate.

WO 97/12581 discloses stable omeprazole granules without any basifying compound. Conventionally, the enteric layer comprises a plasticizer, such as triethyl citrate. The granules can comprise lubricants exhibiting hydrophobic properties. Furthermore, an ionic surfactant, such as sodium lauryl sulfate, or crospovidone, which has an alkaline nature, are combined with the active principle.

WO 98/19668 discloses omeprazole granules, the stability of which is improved by inserting a barrier layer between the enteric coating and the active principle. This barrier layer serves to protect the active principle from ambient moisture and from the enteric polymer, which has an acidic nature. This document does not suggest the use of a hydrophobic substance in the barrier layer but it can comprise SIMETHICONE® ($\alpha$-(trimethylsilyl)-$\omega$-methylpoly[oxy(dimethylsilylene)] mixed with silicon dioxide) in a proportion by mass of 0.4% with respect to the weight of the active principle. MYVACET® (acetylated monoglyceride) is employed as plasticizer in the enteric layer. The granules are composed of an alkaline core which can comprise magnesium, calcium or aluminum hydroxides or oxides, trisodium phosphate or magnesium trisilicate.

The documents of the prior art which relate to solid oral formulations of proton pump inhibitors for which it is desired to increase the stability disclose formulations which comprise hydrophobic substances but these documents do not teach that the hydrophobic substances are of use in increasing the stability on storage. In contrast, in these documents, the hydrophobic substances are used conventionally as plasticizers in the enteric layer (WO 96/01624, WO 97/12581 and WO 98/19668), as lubricant (WO 97/12581) or as binder (WO 98/19668). Furthermore, the compositions which they disclose comprise alkaline compounds or ionic surfactants.

In order to improve the duration of stability on storage of formulations insoluble in gastric fluid comprising a proton pump inhibitor, a proposal has been made, in the prior art, to introduce an alkaline substance and a hydrophobic substance into the formulation.

WO 98/52564 discloses benzimidazole granules comprising an inert nucleus coated with a layer comprising the active principle in combination with an alkaline substance, with a barrier layer composed of a hydrophobic substance, and with an enteric layer. The hydrophobic substance is a polyalkylsiloxane, a mineral oil, isopropyl myristate, stearic acid or cetyl alcohol. The alkaline substance is, for example, ammonia, ammonium hydroxide or ammonium carbonate.

WO 98/52564 provides an improvement to the stability of benzimidazole granules by inserting a hydrophobic film between the active principle and the enteric coating and by using an alkaline substance in combination with the active principle.

There also exist, in the prior art, two documents relating to formulations of a proton pump inhibitor which are not insoluble in gastric fluid, which are not in the form of microgranules and which comprise hydrophobic substances.

WO 96/31213 relates to a pasty oral formulation of a proton pump inhibitor for a veterinary use or for people having difficulty in swallowing. This formulation is stable on long-term storage. It comprises a hydrophobic oily liquid vehicle and a hydrophobic thickening agent. The oily vehicle is, for example, MIGLYOL 810® (caprylic/capric triglyceride). The thickening agent is cetearyl alcohol, liquid paraffin or hydrogenated castor oil. The formulation also comprises basifying agents, such as potassium sorbate or triethanolamine. The teaching of this document is specific to a semisolid formulation.

EP 769 938 discloses prolonged-release soft capsules comprising active substances which are unstable toward moisture, oxidation and gastric fluid.

Conventional soft capsules are mainly composed of a mass of hydrated gelatin and of numerous additives which may prove to be incompatible with the active principle. EP 769 938 guarantees the stability of the soft capsules comprising moisture-sensitive active principles by isolating the active principle from the gelatin body. The soft capsules of EP 769 938 are composed

- of a core comprising the active principle and 70% silicone, coated
- with a first layer composed of gelatin, sorbitol and glycerol, coated
- with a silicone film.

The teaching of EP 769 938 is restricted to soft capsules which are not insoluble in gastric fluid.

There does not exist, in the prior art, a formulation insoluble in gastric fluid formed from microgranules comprising a benzimidazole derivative which is stable on storage, which has no alkaline substances and which comprises a hydrophobic substance, both in the active layer and in the enteric layer.

The aim of the present invention is to provide a formulation insoluble in gastric fluid formed from microgranules of a gastric proton pump inhibitor, with the exception of omeprazole, which has an improved long-term stability on storage and which additionally exhibits the desired therapeutic properties, that is to say a degree of resistance to dissolution in acid medium and a rapid solubility in neutral medium.

The present invention relates to a novel formulation insoluble in gastric fluid of a proton pump inhibitor, with the exception of omeprazole, comprising several hydrophobic substances chosen in order to increase the stability of the active principle while obtaining the desired dissolution profile.

The microgranules which are a subject matter of the present invention advantageously have:

- no alkaline compounds, i.e. the pH of which is greater than or equal to 7, for example amino bases, such as ammonium or triethanolamine; salts of carboxylic acids, such as sodium citrate or potassium sorbate; sodium, aluminum, potassium, magnesium or calcium carbonates, phosphates, hydroxides or oxides; magnesium trisilicate; tris(hydroxymethyl)amino-methane; natural clays, such as montmorillonite; sodium glycerophosphate; sodium borate; organic buffers; or crospovidone;
- no ionic surface-active agents, such as lauryl sulfate, and
- no traces of organic solvents.

The microgranules according to the invention comprise a gastric proton pump inhibitor, with the exception of omeprazole, and each comprise an active layer comprising the active principle and an outer layer for protection in gastric fluid. They are characterized in that the active layer and the layer for protection in gastric fluid each comprise at least one hydrophobic substance chosen in order to increase the stability of the microgranules on storage. The microgranules of the invention have no alkaline compound and no ionic surfactant.

Hydrophobic substances will be chosen which do not react chemically with the active principle, which can be easily processed during the formulation and which are compatible with the excipients used.

In the context of the present invention, the term "hydrophobic substance" is understood to mean any substance which makes it possible to increase the stability of the microgranules on storage, in particular any substance which exhibits an HLB of less than 15, or which is nonhygroscopic, or which is virtually insoluble in water, or which forms a film which is impermeable to water vapor.

In the active layer, the hydrophobic substance preferably represents between 5 and 40% by weight of the active principle. It is advantageously chosen from silicone oils.

It is also possible to include, in the active layer, 5 to 15%, with respect to the weight of active principle of a nonionic surfactant preferably chosen from polysorbates (MONTANOX 80® (polyoxyethylated sorbitan monostearate) or MONTANE 20-60® (sorbitan monolaurate)).

The active layer advantageously comprises a binder chosen from pharmaceutically acceptable binders, for example hydroxypropyl methylcellulose, the proportion by mass of which preferably represents 30 to 50% with respect to the weight of active principle.

The outer layer for protection in gastric fluid is advantageously composed of a film-forming agent for protection in gastric fluid, of a hydrophobic substance and of a hydrophilic plasticizer.

Advantageously, the hydrophobic substance present in the layer for protection in gastric fluid is chosen from the waxes, the oils and their mixtures often used in the pharmaceutical industry, preferably glycerides, for example, GÉLUCIRE® (mixture of glycerol and polyethyleneglycol esters of long fatty acids), in a proportion of 5 to 20% of the dry glaze of the film-forming agent.

The plasticizer is chosen from pharmaceutically acceptable plasticizers, for example PEGs, cetyl alcohol or triethyl citrate.

The plasticizer represents from 5 to 20%, advantageously 10%, of the weight of dry glaze of the film-forming agent.

The film-forming agent insoluble in gastric fluid is advantageously a copolymer of methacrylic acid, such as EUDRAGIT L30D® (methacrylic acid-ethyl acrylate copolymer), in the preparation of 15 to 60% of the dry polymer deposit with respect to the mass of microgranules.

In order to strengthen the resistance to moisture of the layer for protection in gastric fluid, use is optionally made of a lubricating agent chosen from pharmaceutically acceptable lubricants, advantageously talc.

The layer for protection in gastric fluid is advantageously composed of 90 to 95% of film-forming agent and of an equal amount of plasticizer and of hydrophobic substance.

According to a preferred embodiment of the invention, at least one intermediate layer is inserted between the active layer and the layer for protection in gastric fluid. The intermediate layer can also comprise a hydrophobic substance, which preferably represents between 5 and 40% by weight of the active principle.

The intermediate layer can comprise a diluent substance or a coating agent combined with a hydrophobic plasticizer.

According to a preferred embodiment, the microgranules according to the invention comprise:

- a layer of active principle comprising an active principle, a binder chosen from pharmaceutically acceptable binders, a hydrophobic substance and a nonionic surfactant,
- a first protective layer comprising one or more pharmaceutically acceptable hydrophobic diluent substances and a binder chosen from pharmaceutically acceptable binders,
- a second hydrophobic protective layer comprising a coating agent and a hydrophobic plasticizer,
- a layer for protection in gastric fluid comprising an enteric film-forming agent, a hydrophilic plasticizer and a hydrophobic substance.

The first intermediate protective layer advantageously comprises mannitol (which is nonhygroscopic) in a proportion by mass of 100 to 300% and preferably 200% of the weight of the active principle.

This layer also comprises a binder chosen from pharmaceutically acceptable binders, advantageously hydroxypropylmethylcellulose, in a proportion of 10 to 30% and preferably 20% of the weight of mannitol.

It is optionally possible to include, in this protective layer, a lubricant chosen from pharmaceutically acceptable lubricants, in this case talc (which is nonhygroscopic), in a proportion of less than 100% of the weight of the active principle.

The second protective layer is composed of a water-soluble coating agent chosen from pharmaceutically acceptable film-forming agents, advantageously hydroxypropylmethylcellulose, in a proportion of 1 to 10%, preferably 5%, of the weight of microgranules obtained after applying the first protective layer.

Use will advantageously be made, in the second protective layer, of a hydrophobic plasticizer, such as MYVACET® (acetylated monoglyceride), in proportion of 10 to 30% of the dry glaze of the coating agent used.

The second protective layer can comprise a lubricating agent chosen from pharmaceutically acceptable lubricants, such as talc, in a proportion of 10 to 50%, preferably 15%, by weight of the dry glaze of the coating agent used.

According to a preferred embodiment of the present invention, the active layer is applied to a neutral nucleus composed, for example, of sucrose and starch, the diameter of which is between 200 and 900 microns.

The microgranules according to the invention preferably have a particle size of between 0.3 and 3 mm, more preferably between 0.4 and 2 mm.

According to a preferred embodiment, the microgranules of the invention comprise:
35 to 45% of neutral materials,
15 to 25% of mannitol,
5 to 15% of active principle,
8 to 15% of hydroxypropylmethylcellulose,
15 to 60% of a copolymer of methacrylic acid,
0.5 to 1.5% of a silicone oil,
0.5 to 1.5% of a nonionic surfactant,
1 to 6% of a plasticizer,
1 to 6% of a glyceride,
1 to 2% of talc,
the percentages being expressed by mass.

Another subject matter of the present invention is a process for the preparation of the microgranules according to the invention. This process is characterized in that it is carried out in aqueous medium, without the use of any organic solvent.

The microgranules disclosed in the present invention will be obtained by use of any equipment appropriate for the preparation and the coating of microgranules well known to a person skilled in the art and in particular equipment of conventional pan, perforated pan or fluidized air bed type.

According to a preferred embodiment, the microgranules according to the invention are obtained by application to a neutral nucleus, preferably in a fluidized air bed, by successive sprayings:
of an aqueous suspension of active principle and of a hydrophobic substance,
optionally of an aqueous suspension of a diluent substance,
optionally of an aqueous suspension of a coating agent and of a hydrophobic plasticizer, and
of an aqueous suspension of the agent for protection in gastric fluid, also known as enteric film-forming agent.

According to a very particularly valued embodiment, the microgranules according to the invention are applied to a neutral nucleus in a fluidized air bed, by successive sprayings:
of an aqueous suspension of active principle and of a silicone oil,
of an aqueous suspension of mannitol,
of an aqueous suspension of hydroxypropylmethyl-cellulose, and
of an aqueous suspension of the agent for protection in gastric fluid.

Each spraying stage is advantageously followed by sieving and drying at a temperature below the melting point of each of the compounds participating in the composition of the microgranules at said stage.

The microgranules obtained according to this process advantageously comprise less than 1.5%, preferably 0.5%, by weight of water.

A final subject matter of the present invention is the pharmaceutical preparations comprising the microgranules according to the invention capable of being obtained by the process described above; these preparations will advantageously be in the form of hard gelatin capsules comprising 5 to 60 mg approximately of active principle.

Other characteristics and advantages of the present invention will become apparent in the light of the example below.

EXAMPLE

Microgranules are prepared in a fluidized air bed device of Ohlman type, these microgranules having the following composition:

| Composition | Percentage by mass |
| --- | --- |
| Natural materials | 39.3 |
| Lansoprazole | 9.2 |
| PHARMACOAT 630 ® (hydroxyproplmethyl cellulose) | 11.0 |
| Dimethicone | 0.9 |
| Polysorbate 80 | 0.9 |
| Mannitol | 18.3 |
| MYVACET ® (acetylated monoglyceride) | 0.9 |
| Talc | 1.4 |
| EUDRAGIT L30D ® (methacrylic acid-ethyl acrylate copolymer) | 15.0 |
| Triethyl citrate | 1.5 |
| GÉLUCIRE 50/13 ® (mixture of glycerol and polyethyleneglycol esters of long fatty acids) | 1.5 | a) Application of the Principle

The purified water is stirred and the PHARMACOAT 603® hydroxypropylmethyl cellulose) (manufactured by Seppic), the polysorbate 80 (manufactured by Seppic), the dimethicone (manufactured by Lambert et Rivière) and the active principle are successively added.

Stirring of the suspension is maintained throughout the application on the neutral nuclei placed in the fluidized air bed.

The coated neutral materials are subsequently sieved and dried for four hours at approximately 50° C.

b) PHARMACOAT®/Mannitol Preapplication

A preapplication suspension is prepared composed of 4% by weight of PHARMACOAT 603® (hydroxypropylmethyl cellulose), 20% by weight of mannitol 25 (both manufactured by Roquette) and 76% of purified water.

The coated and dried neutral materials obtained above are sprayed with this preapplication suspension.

The preapplied neutral materials are subsequently sieved and then dried for one to four hours at approximately 50° C.

c) PHARMACOAT®/MYVACET® (Hydroxypropylmethyl Cellulose/Acetylated Monoglyceride) Preapplication This preapplication stage is carried out under the same conditions as the PHARMACOAT®/mannitol (hydroxypropylmethyl cellulose/acetylated monoglyceride) preapplication stage.

In the course of stages a), b) and c), the temperature of the granules is maintained between 26 and 28° C. during the spraying of the suspension.

d) EUDRAGIT L30D®/GÉLUCIRE® (Methacrylic Acid-Ethyl Acrylate Copolymer/Mixture of Glycerol and Polyethyleneglycol Esters of Long Fatty Acids) Coating An aqueous coating suspension comprising EUDRAGIT L30D® (methacrylic acid-ethyl acrylate copolymer), triethyl citrate and GÉLUCIERE 50/13® (mixture of glycerol and polyethyleneglycol esters of long fatty acids) is prepared, the GÉLUCIERE® (mixture of glycerol and polyethyleneglycol esters of long fatty acids) manufactured by Gattefossé being added molten at 50° C.

The coated microgranules are subsequently sieved and dried at approximately 45° C. for four hours and then lubricated with talc.

The losses on drying of the microgranules are of the order of 0.5 to 1% after fifteen minutes at 95° C., at the end of each of stages a) to d).

The microgranules obtained have the following properties:

| Content (mg/g) | 91.7 |
|---|---|
| Test of resistance to gastric fluid (% by mass) | |
| after 2 h at pH 1.2 | 4.14 |
| and then for 30 min at pH 6.8 | 82.70 |

In accordance with the European Pharmacopoeia, the in vitro dissolution tests are carried out with a paddle device rotating at a speed of 100 revolutions/minute, in 750 ml of water at 37° C.±0.5° C. and pH=1.2, to which are added, after two hours, 250 ml of an aqueous $Na_3PO_4$ solution at pH=12.5, to obtain 1 l of a solution at pH=6.8.

The invention claimed is:

1. A microgranule comprising a gastric proton pump inhibitor, with the exception of omeprazole, comprising an active layer comprising the proton pump inhibitor and an outer layer for protection in gastric fluid, wherein:
   (A) the active layer is applied to a neutral nucleus;
   (B) the active layer comprises at least one hydrophobic substance chosen from silicone oils and present in the active layer in an amount of between 5 and 40% by weight of the gastric proton pump inhibitor;
   (C) and the layer for protection in gastric fluid comprises at least one hydrophobic substance chosen from glycerides and present in the layer for protection in gastric fluid in an amount of 5 to 20% by weight of the protective layer; and further wherein the microgranule has no alkaline compound and no ionic surfactant.

2. The microgranule as claimed in claim 1, wherein the active layer comprises 5 to 15%, with respect to the weight of proton pump inhibitor, of a nonionic surfactant.

3. The microgranule as claimed in claim 1, wherein the active layer further comprises a binder.

4. The microgranule as claimed in claim 1, wherein the layer for protection in gastric fluid is composed of 90 to 95% of film-forming agent and of 5 to 10% of an equal amount of plasticizer and of hydrophobic substance.

5. The microgranule as claimed in claim 4, wherein the plasticizer represents 5 to 20% by weight of the dry glaze of the film-forming agent.

6. The microgranule as claimed in claim 4, wherein the film-forming agent is from 15 to 60% of the dry polymer deposit with respect to the mass of the microgranule.

7. The microgranule as claimed in claim 4, wherein the film-forming agent is a copolymer of methacrylic acid.

8. The microgranule as claimed in claim 1, which further comprises at least one intermediate layer inserted between the active layer and the layer for protection in gastric fluid.

9. The microgranule as claimed in claim 8, wherein each microgranule comprises:
   (a) an active layer comprising a proton pump inhibitor, a binder chosen from pharmaceutically acceptable binders, a hydrophobic substance and a nonionic surfactant,
   (b) a first protective layer comprising one or more pharmaceutically acceptable hydrophobic diluent substances and a binder,
   (c) a second hydrophobic protective layer comprising a coating agent and a hydrophobic plasticizer, and
   (d) a layer for protection in gastric fluid comprising an enteric film-forming agent, a hydrophilic plasticizer and a hydrophobic substance.

10. The microgranule as claimed in claim 9, wherein the first protective layer comprises mannitol as a diluent substance.

11. The microgranule as claimed in claim 9, wherein the second protective layer is composed of a water-soluble coating agent and of a hydrophobic plasticizer.

12. The microgranule as claimed in claim 1, wherein the active layer is applied to a neutral nucleus and the particle size of the microgranule is between 0.3 and 3 mm.

13. The microgranule as claimed in claim 1, wherein the microgranule comprises: 35 to 45% of neutral nucleus, 15 to 25% of mannitol, 5 to 15% of proton pump inhibitor, 8 to 15% of hydroxypropylmethylcellulose, 15 to 60% of a copolymer of methacrylic acid, 0.5 to 1.5% of a silicone oil, 0.5 to 1.5% of a nonionic surfactant, 1 to 6% of a plasticizer, 1 to 6% of a glyceride, and 1 to 2% of talc, wherein said percentages are expressed by mass.

14. A process for the preparation of the microgranule as claimed in claim 1, wherein said microgranule is prepared in an aqueous medium.

15. A process as claimed in claim 14, wherein the active layer is applied to a neutral nucleus in a fluidized air bed.

16. A pharmaceutical preparation comprising the microgranule as claimed in claim 1, comprising approximately 5 to 60 mg of proton pump inhibitor and a pharmaceutically acceptable carrier.

17. The microgranule as claimed in claim 2, wherein the nonionic surfactant is a polysorbate.

18. The microgranule as claimed in claim 3, wherein the binder is hydroxypropylmethylcellulose.

19. The microgranule as claimed in claim 11, wherein the water-soluble coating agent is hydroxypropylmethylcellulose.

20. The microgranule as claimed in claim 11, wherein the hydrophobic plasticizer is an acetylated monoglyceride.

21. The microgranule as claimed in claim 1, wherein said neutral nucleus has a diameter between 200 microns and 900 microns.

22. A microgranule comprising a gastric proton pump inhibitor, with the exception of omeprazole, comprising an active layer comprising the proton pump inhibitor and an outer layer for protection in gastric fluid, wherein:
   (A) the active layer is applied to a single neutral nucleus;
   (B) the active layer comprises at least one hydrophobic substance chosen from silicone oils and present in the active layer in an amount of between 5 and 40% by weight of the gastric proton pump inhibitor;
   (C) and the layer for protection in gastric fluid comprises at least one hydrophobic substance chosen from glycerides and present in the layer for protection in gastric fluid in an amount of 5 to 20% by weight of the protective layer; and further wherein the microgranule has no alkaline compound and no ionic surfactant.

* * * * *